(12) United States Patent
Hilbert et al.

(10) Patent No.: US 11,105,876 B2
(45) Date of Patent: Aug. 31, 2021

(54) METHOD AND SYSTEM FOR GENERATING SYNTHETIC IMAGES WITH SWITCHABLE IMAGE CONTRASTS

(71) Applicants: SIEMENS HEALTHCARE GMBH, Erlangen (DE); CENTRE HOSPITALIER UNIVERSITAIRE VAUDOIS, Lausanne (CH)

(72) Inventors: Tom Hilbert, Lausanne (CH); Tobias Kober, Lausanne (CH); Patrick Omoumi, Lausanne (CH)

(73) Assignees: Siemens Healthcare GmbH, Erlangen (DE); Centre Hospitalier Universitaire Vaudois, Lausanne (CH)

( * ) Notice: Subject to any disclaimer, the term of this patent is extended or adjusted under 35 U.S.C. 154(b) by 0 days.

(21) Appl. No.: 16/850,188

(22) Filed: Apr. 16, 2020

(65) Prior Publication Data
US 2020/0333414 A1    Oct. 22, 2020

(30) Foreign Application Priority Data

Apr. 16, 2019  (EP) ..................................... 19169543

(51) Int. Cl.
*G01R 33/50*  (2006.01)
*A61B 5/055*  (2006.01)
(Continued)

(52) U.S. Cl.
CPC .............. *G01R 33/50* (2013.01); *A61B 5/055* (2013.01); *G01R 33/4828* (2013.01);
(Continued)

(58) Field of Classification Search
USPC ........................................................ 324/309
See application file for complete search history.

(56) References Cited

U.S. PATENT DOCUMENTS

| 10,712,412 | B2 * | 7/2020 | Hernando ......... G01R 33/5608 |
| 2015/0016701 | A1 | 1/2015 | Jog et al. |
| 2018/0374246 | A1 | 12/2018 | Igarashi et al. |

OTHER PUBLICATIONS

Santyr, Giles E.: "Magnetization Transfer Effects in Multislice MR Imaging", Magnetic Resonance Imaging, vol. 11, pp. 521-532, 1993.

(Continued)

*Primary Examiner* — Rodney E Fuller
(74) *Attorney, Agent, or Firm* — Laurence A. Greenberg; Werner H. Stemer; Ralph E. Locher

(57) ABSTRACT

A system and method generate a synthetic image with switchable image contrast components for a biological object. The method includes: a) using first and second quantitative MRI acquisition techniques for measuring a value of first or second quantitative parameters Q1, Q2 for the biological object and generating first and second quantitative maps, the first and second quantitative MRI acquisition techniques generate first and second contrast-weighted images; b) using the first and second quantitative maps, and the first and second contrast weighted images as inputs in a model configured for generating a synthetic image M with arbitrary sequence parameters P1, P2, P3, according to:

$$M=|C_i f(Q_1,Q_2,P_1,P_2,P_3)|$$

wherein $C_i$ with i=1, 2, are contrast components for the generation of the synthetic image M coming from respectively the first (i=1) and second (i=2) contrast-weighted images (i=1) and f is a function of Q1, Q2, P1, P2 and P3; and c) displaying the synthetic image M.

8 Claims, 2 Drawing Sheets

(51) Int. Cl.
G01R 33/48 (2006.01)
G01R 33/56 (2006.01)
G01R 33/563 (2006.01)

(52) U.S. Cl.
CPC ..... *G01R 33/5601* (2013.01); *G01R 33/5602* (2013.01); *G01R 33/5608* (2013.01); *G01R 33/56341* (2013.01)

(56) References Cited

OTHER PUBLICATIONS

Warntjes J.B.M. et al: "Rapid Magnetic Resonance Quantification on the Brain: Optimization for Clinical Usage", Magnetic Resonance in Medicine, vol. 60, No. 2, pp. 320-329, (2008), XP055400812, ISSN: 0740-3194, DOI: 10.1002/mrm.21635.

Roux M. et al: "Buy one, get two for free: simultaneous knee T2 mapping and morphological analysis on synthetic images using grappatini", Osteoarthritis and Cartilage, vol. 24, (2016), XP029467200, ISSN: 1063-4584, DOI: 10.1016/J.JOCA.2016.01.547.

Marques, Jose P. et al.: "MP2RAGE, a self bias-field corrected sequence for improved segmentation and T1-mapping at high field", NeuroImage, 2010, vol. 49, pp. 1271-1281, doi:10.1016/j.neuroimage.2009.10.002.

Kumar, Neil M. et al.: "Synthetic MRI of the Knee: Phantom Validation and Comparison with Conventional MRI", Radiology, 2018, pp. 1-13, https://doi.org/10.1148/radiol.2018173007.

Hilbert, Tom et al.: "Accelerated T2 Mapping Combining Parallel MRI and Model-Based Reconstruction: GRAPPATINI", J. Magn. Reson. Imaging, 2018, vol. 48 pp. 359-368, DOI: 10.1002/jmri.25972.

Mussard, Emilie et al.: "Accelerated MP2RAGE Imaging Using Sparse Iterative Reconstruction", Advanced Clinical Imaging Technology, Proc. Intl. Soc. Mag. Reson. Med. 24 (2016).

Omoumi, Patrick et al.: "Buy One, Get Two for Free: Simultaneous Knee T2 Mapping and Morphological Analysis on Synthetic Images Using GRAPPATINI", Proc. Intl. Soc. Mag. Reson. Med. 24 (2016).

\* cited by examiner

METHOD AND SYSTEM FOR GENERATING SYNTHETIC IMAGES WITH SWITCHABLE IMAGE CONTRASTS

CROSS-REFERENCE TO RELATED APPLICATION

This application claims the priority, under 35 U.S.C. § 119, of European application EP19169543, filed Apr. 16, 2019; the prior application is herewith incorporated by reference in its entirety.

BACKGROUND OF THE INVENTION

Field of the Invention

The present disclosure is directed, in general, to imaging techniques for imaging biological objects, like tissues, and more specifically to the generation of synthetic images in magnetic resonance imaging (MRI).

Quantitative MRI (qMRI) is becoming a well-established technique especially in musculoskeletal (MSK) research. With the introduction of new acceleration techniques, qMRI is now increasingly feasible to perform in clinical practice. In addition to quantification, qMRI also allows for generating an arbitrary number of synthetic MR image contrasts based on the quantitative masks obtained. This can even offer time savings if synthetic contrasts based on a single parametric map (i.e. a single acquisition) can replace multiple conventional acquisitions. This was exemplarily shown by the use of synthetic images derived from a single T2-mapping sequence which reduced acquisition times compared to individual acquisitions of morphological and quantitative sequences in the conference abstract by Roux et al., Buy One, Get Two for Free: Simultaneous Knee T2 Mapping and Morphological Analysis On Synthetic Images Using GRAPPATINI, Osteoarthritis and Cartilage 24(1): S301-S302 (April 2016). The addition of a T1 map allows for the incorporation of T1-related effects and yields clinically useful MR images.

Typically, synthetic contrasts are generated by applying an analytical signal model to generate a new image: in other words, the analytical signal model is evaluated with the values of the quantitative map(s) for a given set of sequence parameters. For example, a synthetic image S which is T1/T2-weighted can be calculated using the following equation representing the signal model:

$$S = \left| M0 \left( 1 - 2e^{-\frac{TI}{T1}} + e^{-\frac{TR}{T1}} \right) e^{-\frac{TE}{T2}} \right|. \tag{1}$$

The image contrast of the synthetic image S, usually called "synthetic contrast", depends on sequence parameters (inversion time TI, repetition time TR, echo time TE) and tissue properties (longitudinal relaxation T1, transverse relaxation T2, and initial magnetization M0). The sequence parameters can be freely chosen in order to obtain a contrast; typically, they are selected so that the conspicuity of certain image features (e.g. local pathologies like lesions) is optimal. Note that the tissue-related parameters in the signal model (like T1, T2 and M0 in the example above) are given by previously acquired quantitative maps.

Despite of this flexibility of synthetic contrast generation through the creation of synthetic images, clinical acquisition protocols are still able to provide a wider range of image contrasts, especially contrasts mechanisms that are typically generated with preparation modules (e.g., fat saturation, magnetization transfer, MT, off resonance pulses) or sampling strategies (e.g. water-excitation pulses, interleaved slice sampling). These additional weightings (on top of T1/T2/etc.) often affect only certain tissues (i.e. fat tissue in case of fat saturation preparations); this and other physical factors render them hard to synthesize as outlined above. This shortcoming is an important reason why qMRI in combination with synthetic image generation is currently not widely used.

It would hence be desirable to extend synthetic imaging by also modelling additional weighting mechanisms as MT, fat attenuation and others.

To imprint additional contrast information into the synthetic images, the used qMRI method can employ a preparation module during acquisition as it is done in conventional imaging—say, for instance, an MT preparation pulse for additional MT-weighting. This will modify M0 for the different imaged tissue types. Since all images generated with equation (1) depend on M0, all generated synthetic contrasts will be affected. In that way, it is possible to generate different synthetic contrasts (in this example contrasts with additional MT weighting). However, it is not possible to generate contrasts unaffected by the preparation module anymore.

In the example of fat-saturation, the known T1 value of fat can be exploited together with an acquired T1 map to suppress the signal from fat. To that end, the TI in equation (1) is selected such that the signal off fat is close to zero (i.e. TI=ln(2) T1_fat). This type of sequence set-up is typically referred to as Short TI Inversion Recovery (STIR). However, changing the TI in equation (1) not only affects fat tissue but the entire image. In result, the image has an increased T1 weighting and lower signal-to-noise ratio.

BRIEF SUMMARY OF THE INVENTION

It is an objective of the present invention to propose a method and a system for automatically generating synthetic images with switchable image contrast components (e.g. fat suppression, MT-weighting and others) in qMRI that overcome the previously mentioned problems, wherein the method and system are efficient in that they can provide a large variety of contrasts based on short acquisition times on top of a quantitative information.

The objective is achieved according to the present invention by a method and a system for generating synthetic images with switchable image contrasts according to the object of the independent claims. Dependent claims present further advantages of the invention.

The present invention proposes notably a method for generating a synthetic image with switchable image contrast components wherein a first quantitative MRI acquisition technique configured for measuring the value of a first quantitative parameter Q1 for a biological object is used for generating a first quantitative map showing the values of the first quantitative parameter Q1 for the biological object. The first quantitative MRI acquisition technique is configured at the same time for generating at least a first contrast-weighted image with additional contrast weighting (called also hereafter the first contrast) for the biological object and optionally one initial image free of the additional contrast weighting (i.e. pure proton-density image). The method using then a second quantitative MRI acquisition technique configured for measuring a value of a second quantitative parameter Q2 for the biological object and resulting in a second quantitative map showing the values of the second quantitative parameter for the biological object. The second quantitative MRI acquisition technique is configured at the same time for generating at least a second contrast-weighted image with a different additional contrast-weighting (called hereafter the second contrast) for the biological object. According to the present invention, the first contrast-weighted image is preferentially a proton-density image or a quantitative proton-density map with a first proton-density contrast, and the initial image is preferentially a proton-density image free of the additional contrast weighting, and the second contrast-weighted image is preferentially a proton-density image or quantitative proton-density map with a second proton-density contrast being different from the first proton-density contrast, i.e. exhibiting the additional contrast weighting. The method according to the invention uses then the obtained first and second quantitative maps as well as the first and second contrast weighted images, and optionally the initial image, as inputs in a physical (analytical) signal model configured for generating a synthetic image with arbitrary sequence parameters P1, P2, P3 (e.g. TE, TR and TI) wherein each of the first contrast and second contrast might be turned on or off in the synthetic image by interaction with a contrast switch of a user interface when displaying the synthetic image of the biological object, notably through interaction of a user with the contrast switch of the user interface when displaying synthetic images of the biological object. In other words, the present method enables to display a synthetic image of the biological object containing either no contrast or the first and/or second contrasts. The generation of the synthetic image is thus configured for enabling a switching between the first contrast, the second contrast and no contrast. The physical signal model for generating the synthetic image M is in particular given by:

$$M = |C_i f(Q_1, Q_2, P_1, P_2, P_3)| \quad (2)$$

wherein
$C_i$ with i=1, 2, is a contrast weight for the generation of the synthetic image M coming from respectively the first contrast-weighted image (i=1) and the second contrast-weighted image (i=2). $C_i$ will be called hereafter the "contrast component". Preferentially, $C_1$ is the first contrast-weighted image, e.g. a proton-density image with a first proton-density contrast, and $C_2$ is the second contrast-weighted image, e.g. a proton-density image with the second proton-density contrast. Optionally, $C_i$ with i=0, i.e. $C_0$, is the initial image free of the additional contrast weighting, i.e. an image whose intensity corresponds to an image of the biological object free of the additional contrast (e.g. a purely proton density weighted image). f is a function of $Q_1, Q_2, P_1, P_2$ and $P_3$: it is actually a contrast mechanism which depends on the sequence parameters $P_1$ and the quantitative biological object properties. $P_1, P_2, P_3$ are sequence parameters. Q1 and Q2, with Q1 and Q2 being different quantitative parameters (i.e. Q1≠Q2), are the first and second quantitative parameters which represent the quantitative biological object properties. According to the present invention, an activation of the contrast switch is thus configured for automatically switching between the synthetic image M generated by using one of the contrast components $C_i$ and the synthetic image M generated by using another one of the contrast components $C_i$.

In an example, the quantitative maps Q1=T1, Q2=T2 and the sequence parameters P1=TI, P2=TR, P3=TE can be used to create synthetic maps in conjunction with the known contrast mechanisms of relaxation (i.e. T1 and T2):

$$f(Q_1, Q_2, P_1, P_2, P_3) = \left(1 - 2e^{-\frac{P_1}{Q_1}} + e^{-\frac{P_2}{Q_1}}\right) e^{-\frac{P_3}{Q_2}}. \quad (3)$$

The present invention proposes also a system for carrying out the previously described method.

The advantage of the present invention is that it provides a large variety of contrasts based on short acquisition times on top of the quantitative information provided by the quantitative maps (e.g. T1 and T2 values). Especially, it provides to a radiologist the ability to change the contrasts post-acquisition, including the switching between various contrasts effects (e.g. fat on/off) which may help to further improve diagnosis.

The foregoing has outlined rather broadly the features and technical advantages of the present disclosure so that those skilled in the art may better understand the detailed description that follows. In particular, the present invention may help a physician to diagnose a disease for a biological object, which is typically an organ, like a brain.

Additional features and advantages of the disclosure will be described hereinafter that form the object of the claims. Those skilled in the art will appreciate that they may readily use the concept and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

For a more complete understanding of the present disclosure, and the advantages thereof, reference is now made to the following descriptions taken in conjunction with the accompanying drawings, wherein like numbers designate like objects, and in which:

Other features which are considered as characteristic for the invention are set forth in the appended claims.

Although the invention is illustrated and described herein as embodied in a method and a system for generating synthetic images with switchable image contrasts, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
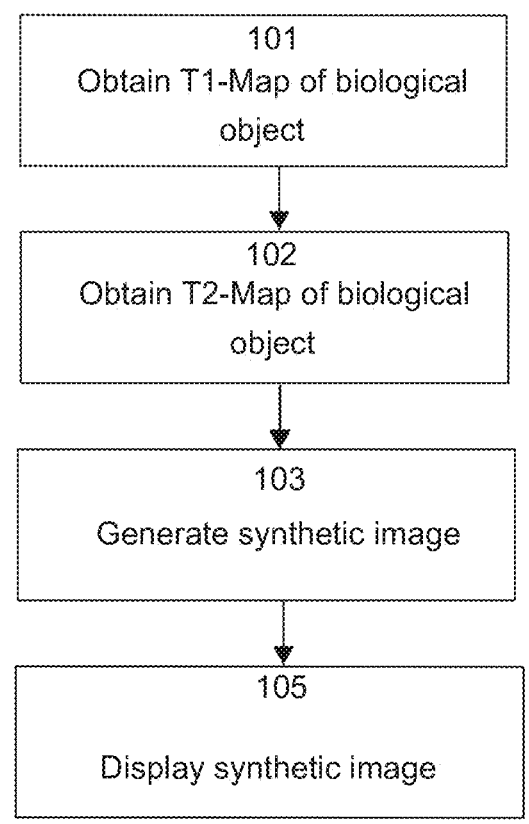
FIG. 1 is a flowchart illustrating a method for contrast switching according to the invention.
Figure 2:
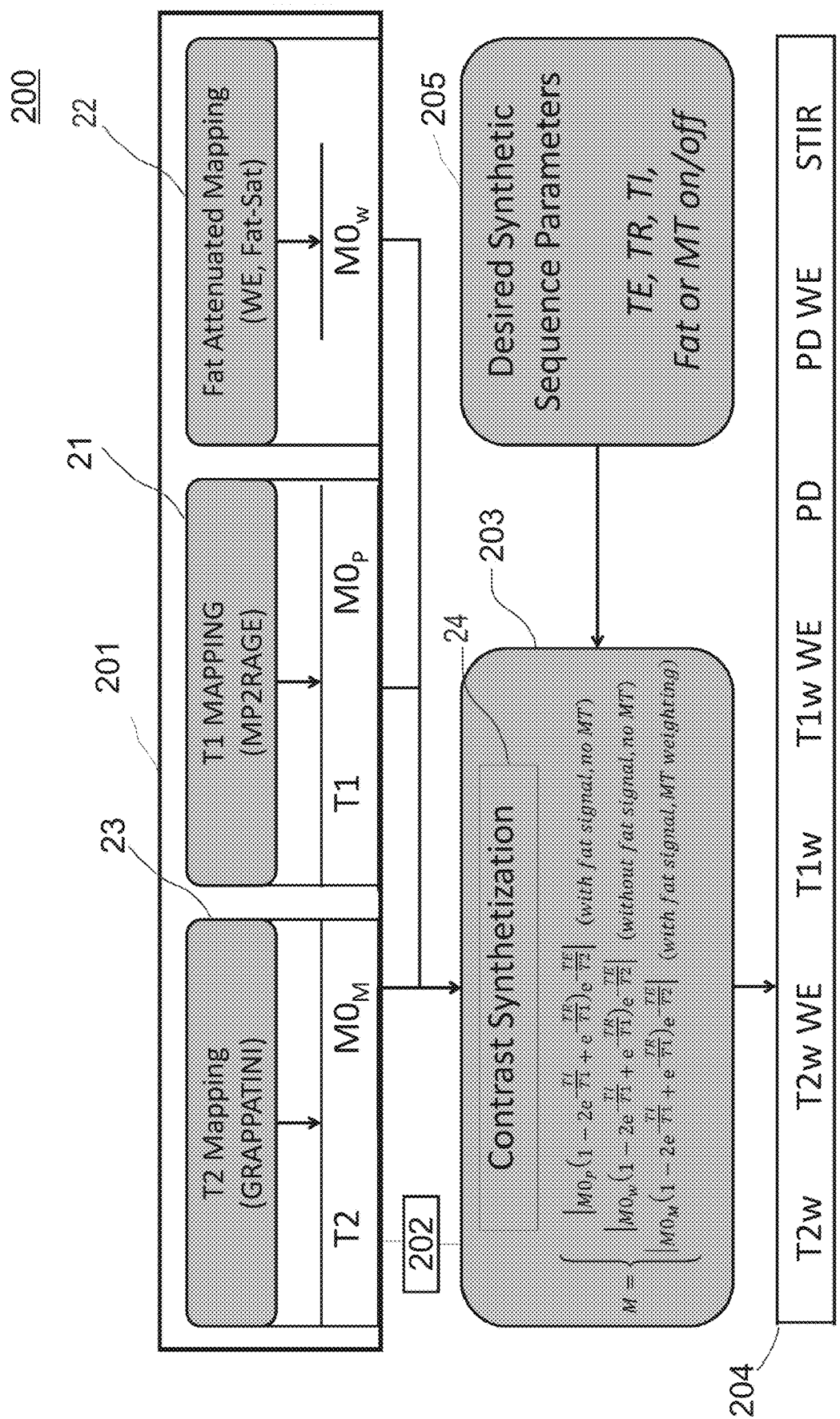
FIG. 2 is an illustration of a system for implementing the claimed method.

FIGS. 1 and 2, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged device. The numerous innovative teachings of the present application will be described with reference to exemplary non-limiting embodiments.

The present invention proposes to use, for the generation of quantitative maps, a quantitative acquisition strategy which measures quantitative parameters in a way that additional contrast information is sampled together with the quantitative parameters for generating a corresponding synthetic (i.e. simulated) image based on physical signal models. While prior art techniques generate synthetic images based on the acquisition of quantitative maps (e.g. T1 and T2 maps) and the use of a physical signal model to generate the synthetic contrasts, the present invention proposes to further improve the existing techniques by using additional weightings. For instance, contrary to prior art techniques, the present invention proposes to automatically obtain and then use different contrast components $C_i$ for generating a synthetic image with a switchable contrast. As previously mentioned, the contrast components $C_i$ are preferentially proton-density (PD)-weighted images (also called "PD-maps" or "M0-maps"), i.e. contrast images wherein the contrast weighting is defined by the number of protons per voxel. M0-maps are typically acquired along with a qMRI acquisition. The contrast components $C_i$ according to the invention, e.g. the M0-maps, comprise therefore additional weightings, like magnetization transfer (MT) and fat suppression, or no weightings. As a result, the contrast components $C_i$ like the M0 maps contain different information (e.g. no additional weighting, attenuated fat signal, MT weighting), which is subsequently used to synthesize image contrasts. The latter can either be performed statically, i.e. generating a fixed set of predefined contrasts (e.g. one image with fat signal, one without), or dynamically, allowing the user to interactively switch additional weightings/suppressions on or off by interaction with the system according to the invention.

We will now describe in more details the method according to the invention through FIG. 1 which describes the different steps of the method 100 carried out by the system according to the invention for enabling a switching between different synthetic contrasts in a synthetic image. The method 100 contains notably the following successive steps, which are preferentially automatically performed by the system according to the invention:

At step 101, the system uses a first quantitative MRI acquisition technique, which is preferentially a T1 mapping acquisition technique, for example a compressed sensing-(CS)-accelerated prototype MP2RAGE (CS-MP2RAGE) acquisition technique characterized by a CS-MP2AGE MRI sequence for obtaining the T1(-weighted) map (i.e. image) of the biological object (see for instance Marques et al., MP2RAGE, A Self-Bias-Field Corrected Sequence for Improved Segmentation and T1-Mapping at High Field, Neuroimage 49(2):1271-1281 (2010)). The first quantitative acquisition technique is configured for measuring a value for a first quantitative parameter, e.g. T1, for the biological object, e.g. a brain. From the use of the first quantitative acquisition technique, the system generates a first quantitative map for the first quantitative parameter, e.g. a T1 map.

According to the present invention, the first quantitative MRI acquisition technique enables at the same time to generate at least a first contrast component which is for instance a first contrast-weighted image for the biological object (e.g. a first proton-density image or quantitative proton-density map) with additional weighting and optionally an initial contrast component, which is for instance an initial image (e.g. a proton-density image or map) free of the additional weighting. For instance, the first contrast-weighted image is a proton-density image $M0_P$ obtained by the system by estimating an initial magnetization of the MP2RAGE sequence used for the generation of the T1 map and which contains an additional weighting (or contrast) like a fat signal. Optionally, the system determines also the initial image which is preferentially a proton-density image or quantitative map free of the additional weighting, i.e. a pure proton-density image or map that is for instance free of fat signal. For this purpose, the system is for instance configured for repeating the same CS-MP2RAGE sequence using a selective water excitation (WE), in order to derive the initial contrast component, e.g. a proton-density image $M0_W$ which is an initial magnetization image without fat signal.

At step 102, the system uses a second quantitative MRI acquisition technique, preferentially a T2 mapping acquisition technique, configured for measuring a value for a second quantitative parameter, e.g. T2, for the biological object. For instance, the system is configured for using a GRAPPATINI sequence as disclosed in Hilbert et al., Accelerated T2 Mapping Combining Parallel MRI and Model-Based Reconstruction: GRAPPATINI, J. Magn. Reson. Imaging. 2018. doi:10.1002/jmri.25972) for acquiring a T2 map of the biological object, the T2 map being the second quantitative map. According to the present invention, the acquisition of the second quantitative map, e.g. T2 map, is also used for acquiring a second contrast component which is a second contrast-weighed image or quantitative map with an additional weighting different from the additional weighting of the first contrast-weighted image or map. Preferentially, the second contrast-weighted image is a second proton-density weighted image or quantitative map for said biological object. For instance, the second proton-density weighted image or map is a MT-weighted image. In that case and preferentially, the system is further configured for using the GRAPPATINI sequence to estimate the initial magnetization $M0_M$ which is MT-weighted, since it uses interleaved slice sampling (see Santyr G E, Magnetization transfer effects in multislice M R imaging, Magn. Reson. Imaging 11(4):521-532 (1993)).

At step 103, the system is configured for using:
a) the first quantitative map, e.g. the T1 map,
b) the second quantitative map, e.g. the T2 map,
c) the first contrast component, which is preferentially the first proton-density image or quantitative proton-density map, e.g. the proton-density image $M0_P$ with fat signal,
d) the second contrast component, which is preferentially the second proton-density image or quantitative proton-density map, e.g. the proton-density image with additional magnetization transfer contrast $M0_M$, and
e) the initial contrast component, which is preferentially the proton-density image or quantitative proton-density map, without fat signal $M0_W$, as inputs in a contrast synthetization module which contains a physical signal model given by Eq. (2), wherein the inputs are used to generate a synthetic image M with arbitrary TE, TR and TI. The system contains a user interface with a contrast switch enabling to automatically switch between the first contrast component, the second contrast component and the initial contrast component (i.e. no contrast—initial image) when displaying, at step 104, a synthetic image of the biological object. Optionally, or alternatively, the system is configured for displaying on a display at least two different contrasts at the same time for the biological object. For instance, the fat signal or MT-weighting could be turned on and off by switching between $M0_P$, $M0_W$, and $M0_M$ when using the following equation for the physical signal model used to generate the synthetic image M by means of the system according to the invention:

$$M = \quad (4)$$

$$\begin{cases} \left| M0_P \left(1 - 2e^{-\frac{TI}{T1}} + e^{-\frac{TR}{T1}}\right) e^{-\frac{TE}{T2}} \right| & \text{(with fat signal, no } MT) \\ \left| M0_W \left(1 - 2e^{-\frac{TI}{T1}} + e^{-\frac{TR}{T1}}\right) e^{-\frac{TE}{T2}} \right| & \text{(without fat signal, no } MT) \\ \left| M0_M \left(1 - 2e^{-\frac{T1}{T1}} + e^{-\frac{TR}{T1}}\right) e^{-\frac{TE}{T2}} \right| & \text{(with fat signal, } MT \text{ weighting)} \end{cases}$$

According to this specific embodiment, at least 3 synthetic images M might be displayed by the system, either at the same time, or by switching from one of the synthetic images to the other one by selecting the appropriate initial magnetization $M0_P$, $M0_W$, or $M0_M$ via the contrast switch.

FIG. 2 illustrates a system 200 for generating synthetic images with switchable image contrasts for a biological object, like a brain. The system contains:
a) a device 201 for acquiring a quantitative map for the biological object, the device being for instance an MRI apparatus 201 configured for acquiring quantitative maps for the biological object, e.g. brain images of a subject;
b) a database 202 or memory for storing data required for creating and storing the synthetic images, the database 202 being for instance connected to the device 201 or part of the latter;
c) a processing unit 203 configured for processing the data required for generating the synthetic image, the processing unit 203 being connected to the device 201 for acquiring imaging data and to the database 202;
d) a display 204 for displaying the synthetic image, the display 204 being connected to the processing unit 203; and
e) the system 200 according to the invention is configured for performing the steps of the previously described method for generating the synthetic image with switchable image contrasts.

The system 200 will be explained now with respect to the specific embodiment involving the acquisition of T1 and T2 quantitative maps, and the generation of $M0_P$, $M0_W$, $M0_M$ images as contrast component $C_i$. The device 201 of the system 200 according to the invention is for instance configured for acquiring first a T1 map 21 using for instance an MP2RAGE sequence, which is further used to estimate a proton-density-weighted image $M0_P$. The same MP2RAGE sequence is used by the device 201 to acquire or estimate a fat attenuated map 22 using for instance the selective WE. Then the device 201 acquires a T2 map 23 using for instance a GRAPPATINI MRI sequence which is further used to estimate the initial magnetization $M0_M$.

The obtained maps and images are then used as input in a contrast synthetization module 24 of the processing unit 203. The contrast synthetization module 24 contains preferentially a physical signal model (contrast mechanism) as shown in Eq. 4 configured for generating a synthetic image M of the biological object from said inputs. The processing unit 203 is further connected to a user interface 205 containing at least one contrast switch that might be for instance activated by a user. According to the present invention, an activation of the contrast switch is configured for switching an image contrast of the synthetic image generated by the contrast synthetization module 24, e.g. switching the Fat and/or MT on or off. In other words, the activation of the contrast switch may automatically change the contrast component $C_i$ used for calculating the synthetic image. Preferentially, the user interface comprises one contrast switch per contrast component for each contrast component $C_i$, with i≥1. The contrast switch is preferentially configured for enabling a switch between a first synthetic image generated by using the contrast component $C_i$, with i≥1, and a second synthetic image generated by using the contrast component $C_0$, in order to switch on/off the corresponding contrast, wherein for the generation of the first and the second synthetic image, the other parameters of the physical signal model remain the same apart the contrast components. Other embodiments may comprise a single contrast switch characterized in that successive activations of the contrast switch successively switch the contrast in the displayed synthetic image by selecting and displaying synthetic images resulting from the use of different contrast components. The user interface 205 is further configured for enabling a user to choose the desired synthetic sequence parameters TE, TR, TI. Consequently, by means of the user interface 25 and its contrast switch, a user may choose to display any of the weighted contrast on a map of the biological object shown then on the display 204 of the system 200, like T2 weighted image, T2 weighted image WE, T1 weighted image, T1 weighted image WE, PD image, PD WE image, or STIR image. Advantageously, the present invention enables therefore a user to switch between different types of preparation contrast in the example by turning the fat signal and a MT-weighting in synthetic contrasts "on" or "off".

The invention was mostly described in the example of MSK imaging with the advantage to turn fat on/off. As before mentioned, the method can also be used to switch between other contrast effects rather than the fat signal. For example, switching MT-weighting or diffusion-weighting on and off. Furthermore, in the described method, the fat information was encoded in the first quantitative map acquisition by using selective WE pulses in one acquisition. Alternatively, the same effect can be achieved by using a fat-saturation preparation module instead. Analogously, the MT information was encoded in the images since the T2 mapping sequence used an interleaved slice sampling technique. In another embodiment, the MT-weighting may be encoded, i.e. acquired or estimated, by using off resonant MT pulses instead.

In the example above, the acquisition strategy for T1 mapping used an MP2RAGE sequence and the acquisition strategy for T2 mapping used a GRAPPATINI sequence. In an alternative embodiment, these sequences may be replaced with other qMRI techniques (e.g. Variable-Flip-Angle Fast Low Angel Shot VFA-FLASH for T1 mapping or T2 prepared FLASH for T2 mapping). Optionally, other quantitative parameters than T1 and/or T2 may be acquired (e.g. T2*, multi compartment T2/T1, MT) while keeping the concept of the invention regarding the switching between contrasts as described above. In other words, when referring to Eq. 2, Q1 and/or Q2 might be chosen among the following quantitative parameters:

T1, T2, T2*, multi-compartment T2/T1, MT, diffusion parameters as FA or ADC, physiological tissue parameters as e.g. myelin content or similar. Notably, the corresponding sequence parameters P1, P2, P3 and contrast mechanism f(Q1,Q2,P1,P2,P3) has to be adapted for each different type of quantitative parameters.

Finally, while the present invention would be of particular interest in MSK applications such as for imaging a knee, it remains also of interest when considering imaging other organs with MRI techniques, for instance for switching the MT signal "on/off" for synthetic images of a brain or switching the fat-signal "on/off" in the field of abdominal imaging.

The invention claimed is:

1. A method for generating a synthetic image with switchable image contrast components for a biological object, the method comprises the steps of:
performing a first quantitative MRI acquisition technique for measuring a value of a first quantitative parameter Q1 for the biological object and generating a first quantitative map of the biological object containing values of the first quantitative parameter Q1 for the biological object, wherein the first quantitative MRI acquisition technique is configured for generating at least a first contrast-weighted image for the biological object;
performing a second quantitative MRI acquisition technique for measuring a value of a second quantitative parameter Q2 for the biological object and generating a second quantitative map of the biological object containing values of the second quantitative parameter Q2 for the biological object, wherein the second quantitative MRI acquisition technique is configured for generating at least a second contrast-weighted image for the biological object;
using the first and second quantitative maps obtained, and the first and second contrast weighted images as inputs in a physical signal model configured for generating a synthetic image M with arbitrary sequence parameters P1, P2, P3, according to:

$$M = |C_i f(Q_1, Q_2, P_1, P_2, P_3)|$$

wherein:
$C_i$ with i=1, 2, are contrast components for a generation of the synthetic image M coming from respectively the first contrast-weighted image (i=1) and the second contrast-weighted image (i=2); and
f is a function of Q1, Q2, P1, P2 and P3 representing a contrast mechanism depending on the arbitrary sequence parameters Pi and quantitative biological object properties provided by Qi; and
displaying the synthetic image M generated by using one of the contrast components $C_i$, wherein an activation of a contrast switch is configured for automatically displaying the synthetic image M generated by using another one of the contrast components $C_i$.

2. The method according to claim 1, which further comprises providing an initial contrast component $C_0$ (i=0) coming from an initial image of the biological object free of a first contrast.

3. The method according to claim 1, wherein the contrast components $C_i$ are proton density maps of the biological object.

4. The method according to claim 1, wherein the first quantitative map is a T1 map and the second quantitative map is a T2 map, the first quantitative parameter Q1 and the second quantitative parameter Q2 being respectively T1 and T2, and wherein $f(Q_1, Q_2, P_1, P_2, P_3)$ is given by $$f(Q_1, Q_2, P_1, P_2, P_3) = \left(1 - 2e^{-\frac{P1}{Q1}} + e^{-\frac{P2}{Q1}}\right)e^{-\frac{P3}{Q2}}$$

with the arbitrary sequence parameters P1=TI, P2=TR, P3=TE.

5. The method according to claim 4, wherein $C_1$ is a proton-density image $M0_F$ with fat signal weighting, $C_2$ is a proton-density image $M0_M$ with magnetization transfer weighting and $C_0$ is a purely proton-density image without fat signal $M0_W$.

6. The method according to claim 1, wherein the first or the second quantitative parameter is one of the following quantitative parameters:
T2*;
a multi-compartment T2/T1;
a magnetization transfer (MT);
diffusion parameters; and
a physiological tissue parameter.

7. The method according to claim 6, wherein:
the diffusion parameters are one of FA or ADC; and
the physiological tissue parameter is a myelin content.

8. A system for generating, for a biological object, a synthetic image with a switchable image contrast component, the system comprising:
a device configured for acquiring a quantitative map of the biological object;
a database for storing data required for creating and storing the synthetic image;
a processor having a contrast synthetization module configured for generating the synthetic image;
a display for displaying the synthetic image;
a user interface containing a contrast switch for switching the switchable image contrast component;
the system is configured for performing a method for generating the synthetic image with the switchable image contrast components for the biological object, the method comprises the steps of:
performing a first quantitative MRI acquisition technique for measuring a value of a first quantitative parameter Q1 for the biological object and generating a first quantitative map of the biological object containing values of the first quantitative parameter Q1 for the biological object, wherein the first quantitative MRI acquisition technique is configured for generating at least a first contrast-weighted image for the biological object;
performing a second quantitative MRI acquisition technique for measuring a value of a second quantitative parameter Q2 for the biological object and generating a second quantitative map of the biological object containing values of the second quantitative parameter Q2 for the biological object, wherein the second quantitative MRI acquisition technique is configured for generating at least a second contrast-weighted image for the biological object;
using the first and second quantitative maps obtained, and the first and second contrast weighted images as inputs in a physical signal model configured for generating a synthetic image M with arbitrary sequence parameters P1, P2, P3, according to:

$$M = |C_i f(Q_1, Q_2, P_1, P_2, P_3)|$$

wherein:
$C_i$ with i=1, 2, are contrast components for a generation of the synthetic image M coming from respectively the first contrast-weighted image (i=1) and the second contrast-weighted image (i=2); and
f is a function of Q1, Q2, P1, P2 and P3 representing a contrast mechanism depending on the arbitrary sequence parameters Pi and quantitative biological object properties provided by Qi; and displaying the synthetic image M generated by using one of the contrast components $C_i$, wherein an activation of said contrast switch is configured for automatically displaying the synthetic image M generated by using another one of the contrast components $C_i$.

\* \* \* \* \*